United States Patent [19]

Reimann et al.

[11] 4,056,616

[45] Nov. 1, 1977

[54] ROSAMICIN DERIVATIVES AND METHOD OF USING SAME

[75] Inventors: Hans Reimann, Wayne; Robert S. Jaret, Livingston; Mohammad Mehdi Nafissi-Varchei, North Caldwell, all of N.J.

[73] Assignee: Schering Corporation, Kenilworth, N.J.

[21] Appl. No.: 664,204

[22] Filed: Mar. 5, 1976

[51] Int. Cl.$^2$ .................. A61K 31/71; C07H 17/08
[52] U.S. Cl. .................. 424/180; 424/181; 536/17
[58] Field of Search .................. 536/17; 424/180, 181

[56] References Cited

U.S. PATENT DOCUMENTS 3,769,273  10/1973  Massey et al. .................. 536/17
3,975,372  8/1976  Ganguly et al. .................. 536/17

OTHER PUBLICATIONS

Tsukiura et al., "The Jour. Of Antibiotics", vol. XXII, No. 3, 1969, pp. 100–105.
Wagner et al., "The Jour. Of Antibiotics", vol. XXV, No. 11, 1972, pp. 641–643.

*Primary Examiner*—Johnnie R. Brown
*Attorney, Agent, or Firm*—Stephen B. Coan; Raymond McDonald; Carver C. Joyner

[57] ABSTRACT

Rosamicin is an antibiotic elaborated by *Micromonospora rosaria*. The compounds described herein are antibacterial derivatives of rosamicin. Also described are processes for the preparation of these antibacterial derivatives from rosamicin.

51 Claims, No Drawings

ROSAMICIN DERIVATIVES AND METHOD OF USING SAME

This application is a continuation-in-part of copending application Ser. No. 554,250, filed Feb. 28, 1975, now abandoned.

This invention relates to novel antibacterial agents derived from rosamicin. More particularly, this invention relates principally but not exclusively to antibacterial agents formed when rosamicin is converted to its 12,13-desepoxy-12,13 dehydro analog and to simple derivatives thereof. This invention also relates to processes for preparing such compounds.

DESCRIPTION OF THE PRIOR ART

Rosamicin, formerly known as Antibiotic 67-694 which antibiotic and certain derivatives thereof are described in British Pat. No. 1,302,142 granted May 2, 1973 entitled, *Antibiotic 67-694 and Methods For Production Thereof*. Rosamicin is elaborated by *Micromonospora rosaria* which is also described in the aforementioned British patent. Rosamicin has the following structural formula:

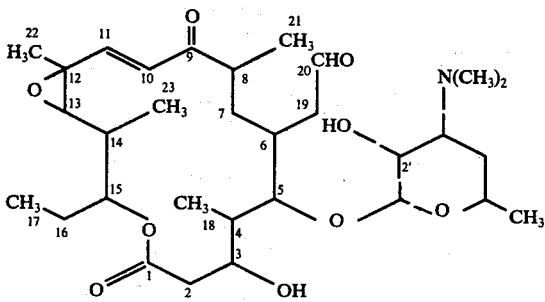

As can be seen from Formula I, rosamicin is a dihydroxy compound having one hydroxyl group at the 3-position of the macrolide ring and another at the 2'-position of the glycosidically linked sugar moiety. Both hydroxyl groups are susceptible to esterification. However, it is the group at the 2'-position which is first to react. Thus, in order to form a 3-monoester, it is necessary to esterify both hydroxyl groups and employ a selective hydrolysis to remove the 2'-ester function. Such a hydrolysis is described in South African Patent No. 74/8630 granted Aug. 16, 1974 entitled: *Novel Monoesters of Rosamicin*.

The novel hydrolysis process is equally applicable to the 3,2'-diesters of the compounds of this invention.

DESCRIPTION OF THE INVENTION

This application is directed to the derivatives of rosamicin depicted by the structural formulae set forth below:

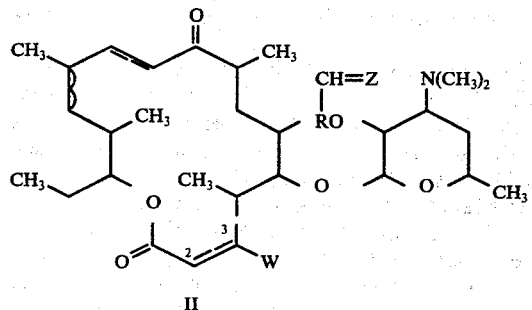

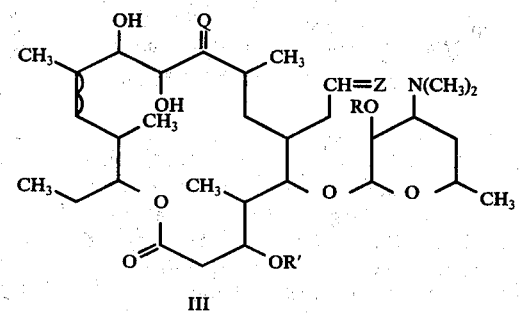

and the non-toxic pharmaceutically acceptable acid addition salts thereof wherein the dotted lines represent facultative double bonds; Q is a member selected from the group consisting of O, and

Z is a member selected from the group consisting of O,

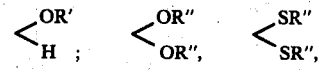

NOR' and NOR"; R and R' are members selected from the group consisting of hydrogen and hydrocarbon carbonyl having 2 to 18 carbon atoms; R" is hydrogen or alkyl having 1 to 5 carbon atoms; B, together with the carbon atoms of positions 12 and 13 to which it is attached, represents a single bond or a double bond or, when Q or Z is other than O, or when the macrolide ring is saturated between positions 10 and 11 or unsaturated between positions 2 and 3, B may also be an oxirane ring; and W is a member selected from the group consisting of OR' and hydrogen, R' being as previously defined with the proviso that when positions 2 and 3 are connected by a double bond, W is hydrogen; and the further proviso that in formula II, when B together with the carbon atoms to which it is attached represents a double bond, W is OR', Q is O, and positions 10 and 11 are connected by a double bond, Z is other than

As used herein, the bonds connecting the various substituents to the macrolide ring may be in any of the possible stereochemical configurations. In like manner, this application includes both the cis and trans forms of 12, 13-desepoxy-12, 13-dehydrorosamicin, and of compounds derived therefrom.

Thus, in its composition of matter aspect, this invention resides in rosamicin derivatives wherein one or more of positions 2, 2', 3, 9, 10, 11, 12, 13 and 20 are modified and derivatized.

In its preferred composition of matter aspect this invention resides in 12,13-desepoxy-12,13-dehydrorosamicin including non-toxic pharmaceutically acceptable acid addition salts, non-toxic pharmaceutically acceptable esters and non-toxic pharmaceutically acceptable acid addition salts of said esters.

In another of its composition of matter aspects, this invention resides in 9-dihydrorosamicin and 9-dihydro-12,13-desepoxy-12,13-dehydrorosamicin including non-toxic pharmaceutically acceptable acid addition salts, non-toxic pharmaceutically acceptable esters and non-toxic pharmaceutically acceptable acid addition salts of said esters.

As used herein non-toxic pharmaceutically acceptable acid addition salts denote those generally employed in the pharmaceutical art. Embraced by the term are the salts formed with inorganic acids such as sulfuric, phosphoric and hydrohalic (e.g. hydrochloric) and those formed with carboxylic acids having 2 to 18 carbon atoms such as aliphatic, cycloaliphatic, aromatic and heterocyclic carboxylic acids including dicarboxylic acids. Exemplary of such acids are acetic, propionic, stearic, tartaric, maleic, cyclopropylcarboxylic, cyclopentylcarboxylic, adamantoic, furoic, nicotinic, thenoic, picolinic, benzoic, phenylacetic and the like. A preferred class of non-toxic pharmaceutically acceptable acid addition salts are alkyl sulfate salts wherein the alkyl group contains 10 to 18 carbon atoms.

In like manner, the non-toxic pharmaceutically acceptable esters of this invention also embrace esters of the acids generally used in the pharmaceutical arts and includes esters of carboxylic acids having 2 to 18 carbon atoms. Embraced by the term are aliphatic, cycloaliphatic, aromatic and heterocyclic including the hemi esters formed with dicarboxylic acids such as maleic, malic, malonic acids and the like. Examples of such acids are set forth herein above as those suitable for preparing pharmaceutically acceptable acid addition salts, excluding those used to prepare alkyl sulfate salts.

In those instances wherein a compound of this invention has a 2'-and a 3-hydroxyl group esterified, this invention also embraces mixed esters. For example, 12,13-desepoxy-12,13-dehydrorosamicin may be esterified at the 2'-position with an acylating agent derived from one hydrocarbon carboxylic acid, and subsequently, esterified at the 3-position with an acylating agent derived from a different hydrocarbon carboxylic acid.

In one of its process aspects, this invention resides in a method for converting rosamicin to the corresponding 12,13-desepoxy-12,13-dehydro analog by treating rosamicin with an alkali metal iodide in an organic acid at above ambient temperatures.

In another of its process aspects, this invention resides a method for converting a rosamicin or a 12,13-desepoxy-12,13-dehydro or a 10,11-dihydro derivative thereof to the corresponding 20-oxime by treating rosamicin or said derivative with hydroxylamine.

In yet another of its process aspects, this invention resides in a method for converting rosamicin or a 12,13-desepoxy-12,13-dehydro or a 10,11-dihydro derivative thereof to the corresponding 20-dihydro analog by treating rosamicin or said derivative with a mild reducing agent, such as lithium aluminum tri-t-butoxyhydride.

In a still further process aspect, this invention resides in preparing alkyl sulfate acid addition salts of the compounds of this invention from their respective free nitrogen bases wherein the alkyl group contains 10 to 18 carbon atoms.

The following reaction sequences are set forth to illustrate both the process aspect and the composition of matter aspect of this invention. These sequences and the specific examples which follow, are not to be construed as limiting the scope of this invention.

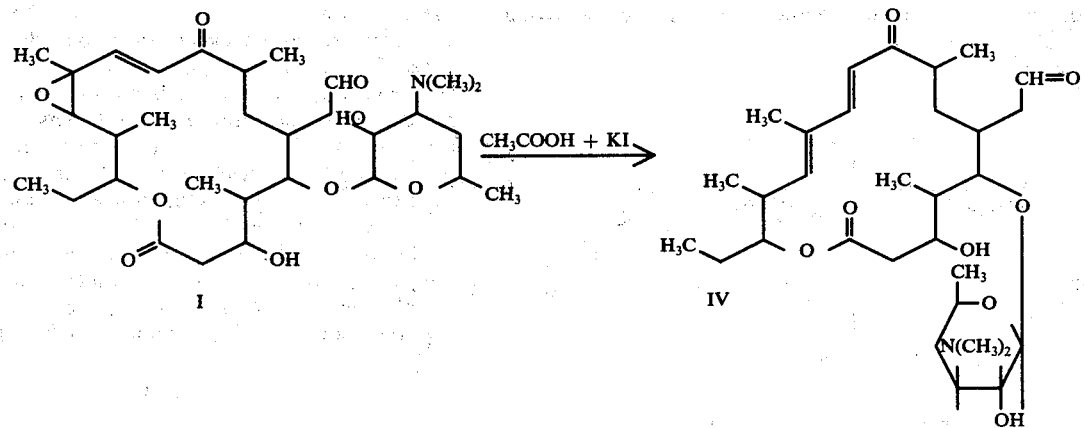

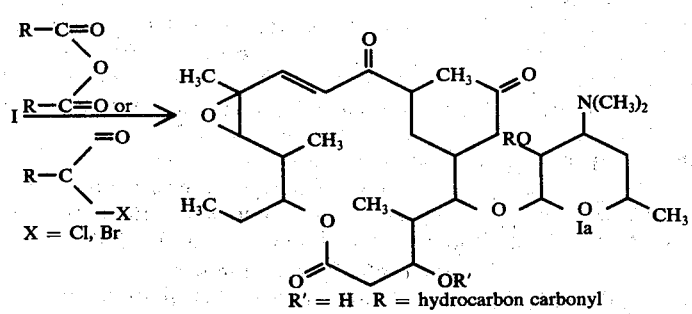

-continued
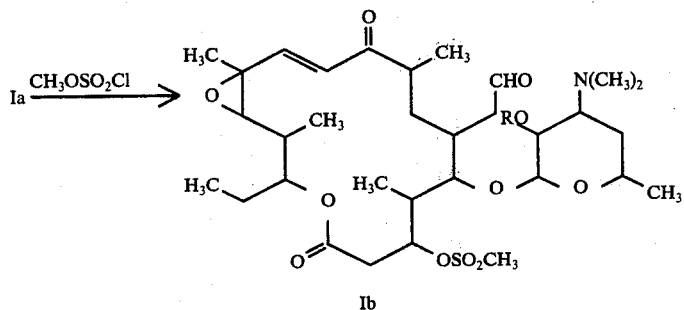
Ib
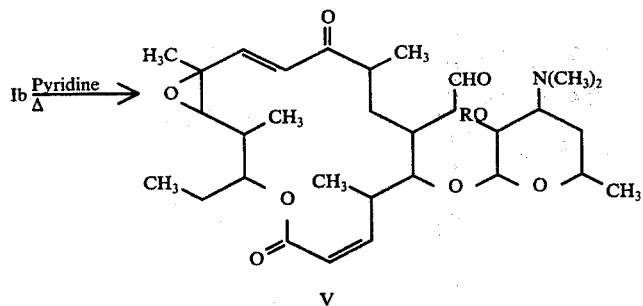
V
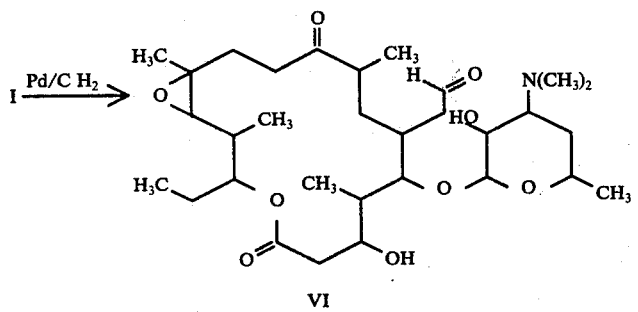
VI
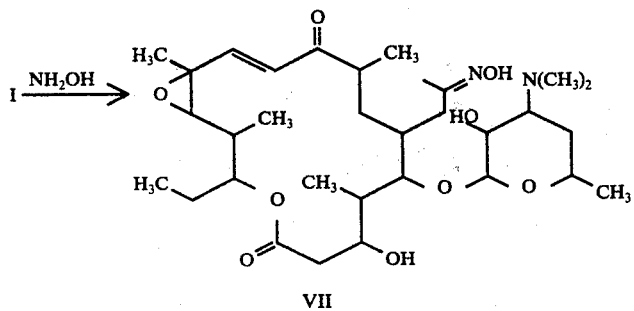
VII
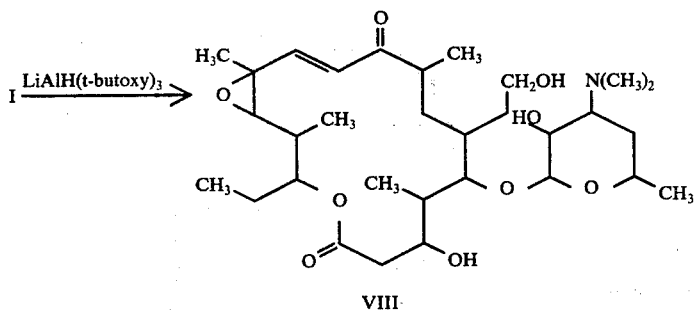
VIII -continued
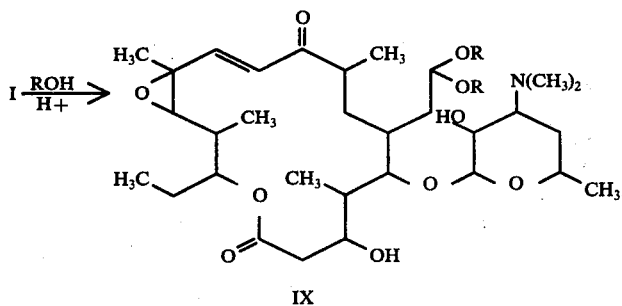
IX
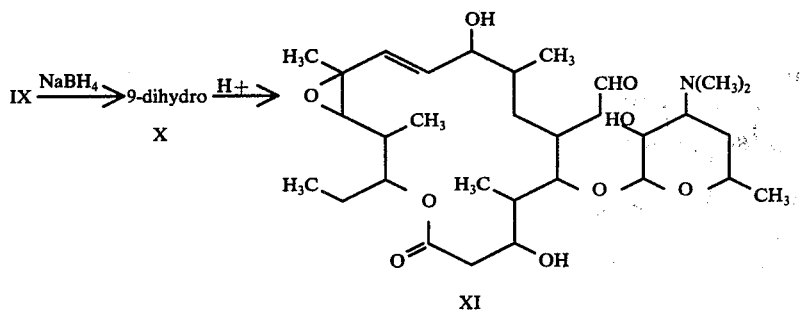
XI
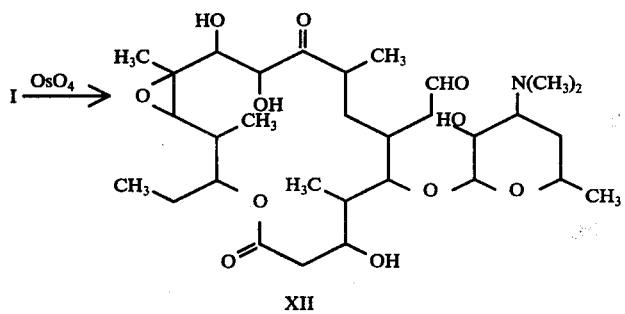
XII
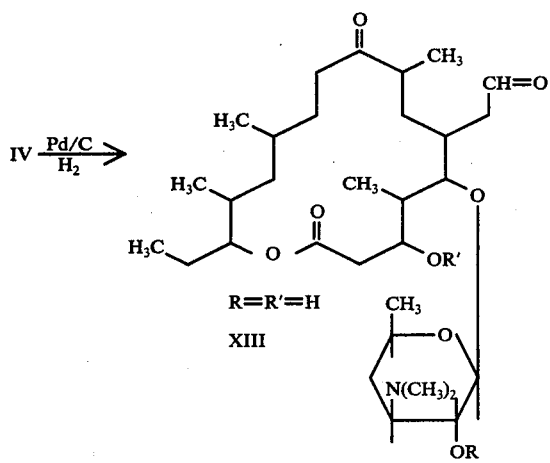
R=R'=H
XIII
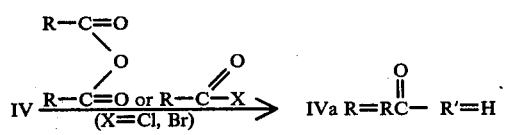
IVa R=RC—  R'=H
IVb 3-methanesulfonate-2'-mono-ester of IV -continued
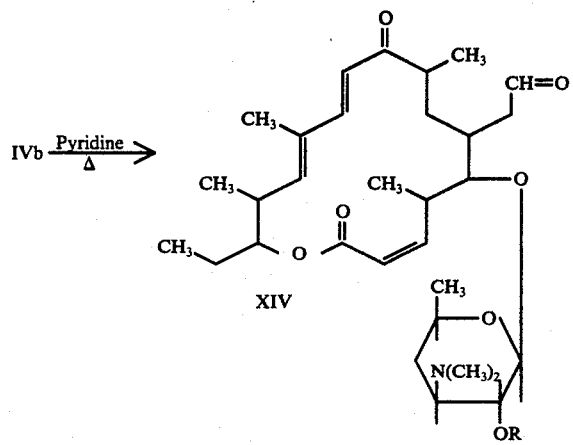
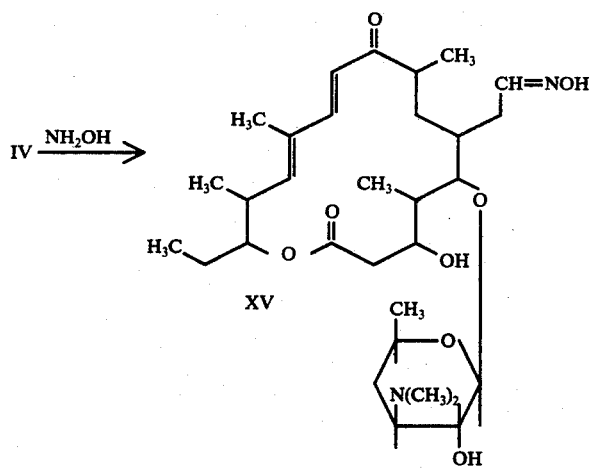
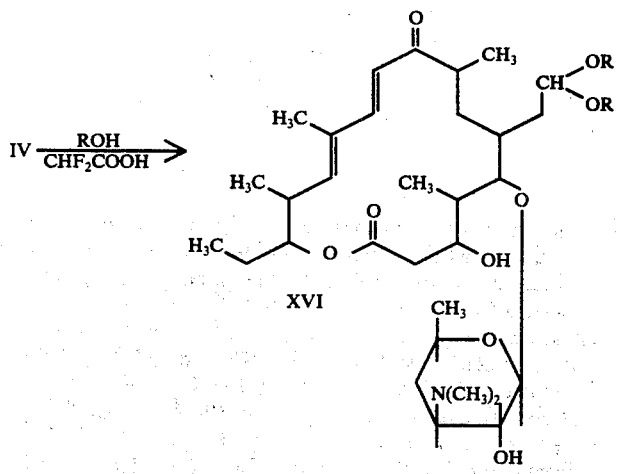

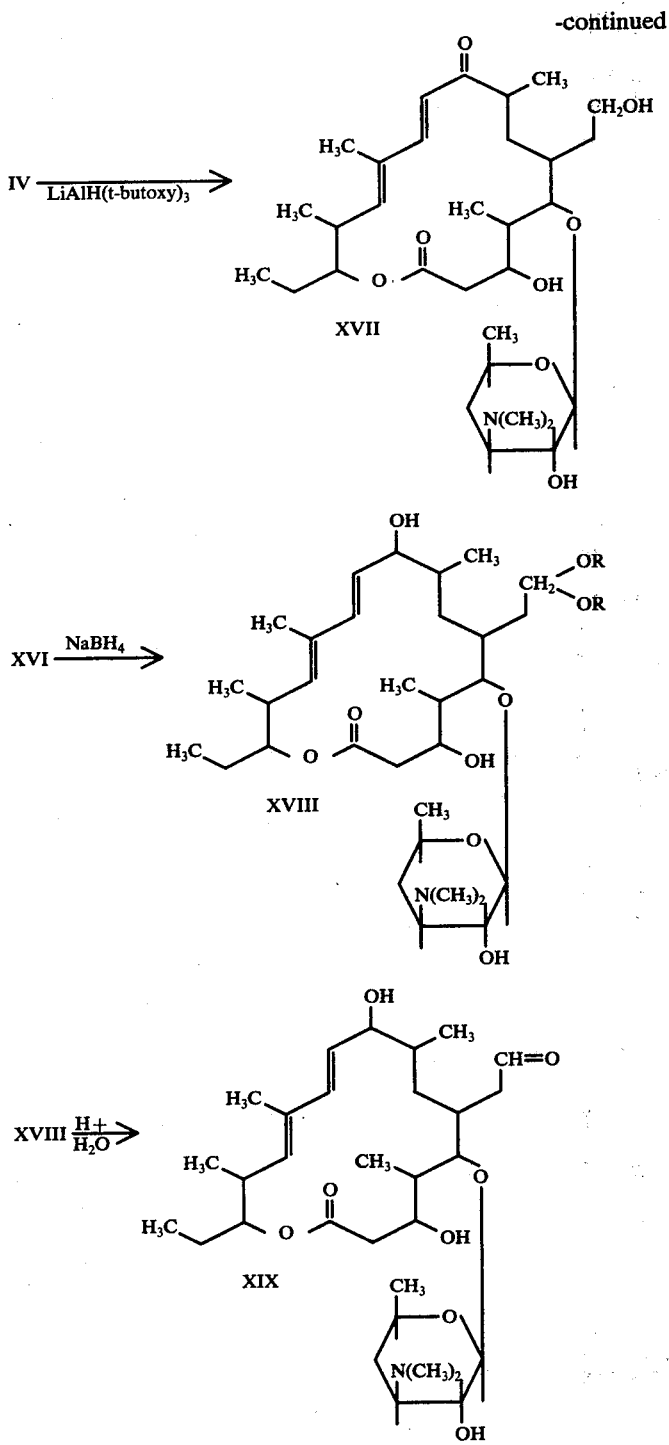

Rosamicin (formula I) may be subjected to a plurality of reactions to provide novel derivatives. The Reaction Sequences set forth schematically on the preceding pages describe the syntheses of the novel products of this invention, which products are antibacterial agents. Further, the products of these Reaction Sequences often differ from rosamicin with respect to potency, spectrum of activity and the mode of administration to which they (the reaction products) are best suited. Moreover, many of these reaction products are susceptible to being converted into still other antibacterial agents. Since antibacterial agents of this class, i.e. macrolides, are usually administered in the form of acid addition salts, or of hydrocarbon carboxylic acid esters or of acid addition salts of such esters these simple derivatives are by implication included in the product aspect of this invention.

Rosamicin upon being subjected to treatment with an alkali metal iodide in an organic acid; or upon being treated with phosphorous trialkoxides, trialkyl phosphines, triphenyl phosphines or hexalkyl phosphoimidates, is converted to 12,13-desepoxy-12,13-dehydrorosamicin (IV). A preferred medium for effecting this reaction is potassium iodide in refluxing acetic acid. The reaction product may be advantageously isolated by diluting the reaction mixture with ice water, extracting the product with a water immiscible organic solvent, washing the extract and isolating the product therefrom.

By hydrogenating rosamicin in a neutral solvent using a noble metal catalyst, preferably palladium on charcoal, 10,11-dihydrorosamicin (VI) is prepared. Under substantially the same conditions 12,13-desepoxy-12,13-dehydrorosamicin (IV) is converted to 12,13-desepoxy-10,11-dihydrorosamicin (XIII).

A 2'-monoester of rosamicin (Ia) treated with an alkyl or aralkyl sulfonyl halide, preferably methanesulfonyl chloride in the presence of a tertiary amine, preferably pyridine is converted to the corresponding 3-methanesulfonate (Ib) which when heated in the presence of a tertiary amine, e.g. pyridine is converted to the 2,3-dehydro analog (V). The 2'-monoesters of rosamicin derivatives may also be converted to their respective 2,3-dehydro analogs by the foregoing reaction sequence. Exemplary of such derivatives are the 2'-monoesters of the following: 12,13-desepoxy-12,13-dehydrorosamicin;12,13-desepoxy-10,11-dihydrorosamicin; 20-dihydrorosamicin and 10,11-dihydrorosamicin. For example, the reaction sequence IV→IVa→IVb→XIV sets forth the conversion of such a derivative to its 2,3-dehydro analog.

Rosamicin (I) or derivatives thereof wherein the 20-aldehyde moiety is intact may be converted to the corresponding aldoxime by treatment with hydroxylamine, preferably in an alcoholic medium at elevated temperatures. This reaction is exemplified by the conversion of compound (IV) to compound (XV). It is also exemplified by the conversion of rosamicin (I) to rosamicin-20-oxime (VII). These same compounds, i.e. those having an intact aldehyde moiety, may be converted to the corresponding carbinol by reduction with a mild reducing agent; lithium aluminum tri-t-butoxyhydride being preferred. This reaction is exemplified by the conversion of compound (IV) to its 20-dihydro analog compound (XVII). The reaction is further exemplified by the conversion of rosamicin (I) to 20-dihydrorosamicin (VIII).

Rosamicin I may be converted to a 20-di-lower-alkyl acetal (e.g. compound IX) by treatment with a lower alcohol such as methanol, ethanol, propanol or the like in the presence of an acid catalyst, preferably difluoroacetic acid. The so-produced 20-di-loweralkyl acetal may then be reduced at position 9, preferably with sodium borohydride in an alcoholic medium to yield the corresponding 9-dihydro analog of rosamicin or of its respective derivatives. Hydrolysis of the thus produced 9-dihydro-20-di-loweralkyl acetal in an aqueous medium in the presence of an acid catalyst (e.g. trifluoroacetic acid) affords 9-dihydrorosamicin XI. Derivatives of rosamicin having the 20-aldehyde function intact may be subjected to the same reaction sequence to yield the corresponding 9-dihydro analog. Exemplary of the foregoing, is the conversion of compound IV to compound XVI to compound XVIII thence to 9-dihydro-12,13-desepoxy-12,13-dehydrorosamicin (XIX).

Although the reactions set forth above have, for the most part, been shown utilizing rosamicin or 12,13-desepoxy-12,13-dehydrorosamicin, it should be apparent to those skilled in the art that Q,Z,R and R' substituted analogs may be employed in many of the reactions shown. Further, in those instances wherein analogs may not be employed in the reaction sequences, they may be prepared by using the product of said sequences. For example, in the transformation of rosamicin I to 12,13-desepoxy-12,13-dehydrorosamicin IV, R or R' substituents at positions 2',3 would be partially hydrolyzed during the isolation procedure. Thus, if the desired product was to have such a substituent, it could advantageously be added to 12,13-desepoxy-12,13-dehydrorosamicin at the end of the transformation. Conversely, if a Z,R,R'-substituted 10,11-dihydrorosamicin analog is being prepared, then an appropriately Z, R, R' substituted rosamicin may be employed in the transformation to yield the desired compound directly.

EXAMPLE 1

12,13-Desepoxy-12,13-dehydrorosamicin

Heat a solution of 15 g of potassium iodide in 30 ml of acetic acid to reflux temperature. Add dropwise a solution of 6 g of rosamicin in 18 ml of acetic acid and continue heating the mixture under reflux for 55 min. Cool the solution and pour into about 180 g of ice, then adjust to about pH 9 with 10% aqueous sodium hydroxide. Extract with ethyl acetate and wash the organic extracts with alkaline sodium thiosulfate solution and with water. Concentrate the organic solution to a residue containing the title compound.

A. Chromatograph the residue on silica gel, eluting with 3% methanol in chloroform. Combine fractions containing a single compound on the basis of thin layer chromatography, concentrate and crystallize from chloroform-hexane to obtain the compound of this example. Dry to constant weight, m.p. 109°–111°, $[\alpha]_D -33°$ (ethanol), $\lambda_{max}^{MeOH}$ 283 nm ($\epsilon$21,700). On the basis of nuclear magnetic resonance and nuclear Overhauser effect experiments this compound is assigned the 12,13-trans stereochemistry.

B. Continue elution of the chromatographic column with the same solvent system to obtain fractions containing the compound described above in admixture with a more polar component. Combine these fractions and rechromatograph on silica gel using the same solvent system. Elute and combine fractions on the basis of thin layer chromatography to obtain an additional quantity of the compound described above. Continue the elution to obtain fractions containing the minor, more polar component. Combine these fractions and concentrate to a residue of the compound, $[\alpha]_D + 34°$ (ethanol), $\lambda_{max}^{MeOH}$ 288 nm ($\epsilon$14,300). On the basis of nuclear magnetic resonance and nuclear Overhauser effect experiments this compound is assigned the 12,13-cis stereochemistry.

EXAMPLE 2

12,13-Despoxy-12,13-dehydrorosamicin stearate salt

Dissolve 100 mg of 12,13-desepoxy-12,13-dehydrorosamicin (trans isomer) in 5 ml of ethanol. Add a solution of 50 mg of stearic acid in 5 ml of ethanol with stirring. Concentrate the solution to a residue under reduced pressure and dry under high vacuum to obtain the compound of this example, $[\alpha]_D -18°$ (ethanol), $\lambda_{max}^{MeOH}$ 283 nm ($\epsilon$22,000).

EXAMPLE 3

12,13-Desepoxy-12,13-dehydrorosamicin potassium dihydrogen phosphate salt

Add 100 mg of 12,13-desepoxy-12,13-dehydrorosamicin (trans isomer) to a solution of 24 mg of potassium dihydrogen phosphate in 25 ml of water. Stir the mixture for 30 min., filter and lyophilize to obtain the desired salt, m.p. 107°-112°, $[\alpha]_D-17°$ (water), $\lambda_{max}^{MeOH}$ 283 nm ($\epsilon$21,000).

EXAMPLE 4

12,13-Desepoxy-12,13-dehydrorosamicin-2'-propionate

Dissolve 100 mg of 12,13-desepoxy-12,13-dehydrorosamicin (trans isomer) in 25 ml of acetone and add a total of 0.175 ml of propionic anhydride in several portions over a period of three days. Keep the solution at room temperature for an additional day, then evaporate the solvent and triturate the residue with cold dilute ammonium hydroxide. Isolate the product by filtration and purify by dissolving in chloroform and filtering the solution through a short column of silica gel. Concentrate the eluate to a residue and obtain thereby the compound of this example, m.p. 90°-94°, $\lambda_{max}^{MeOH}$ 283 nm ($\epsilon$20,800), mass spectrum M+ 621.

EXAMPLE 5

12,13-Desepoxy-12,13-dehydrorosamicin-2'-acetate

Dissolve 1.13 g of 12,13-desepoxy-12,13-dehydrorosamicin (trans isomer) in 15 ml of acetone and add 240 mg of acetic anhydride. Stir at room temperature for 15 hr., then evaporate the solvent under reduced pressure and triturate the residue with dilute ammonium hydroxide solution. Extract with ethyl acetate, wash the extracts with water and dry over sodium sulfate. Evaporate the solvent under reduced pressure to obtain the crystalline product of this example, m.p. 120°-121°, $[\alpha]_D-5°$ (ethanol).

In a similar manner, by substituting equivalent amounts of other anhydrides, such as butyric, valeric, hexanoic, octanoic and the like, for the acetic anhydride in the above procedure, the corresponding esters are obtained.

EXAMPLE 6

12,13-Desepoxy-12,13-dehydrorosamicin-2'-benzoate

Dissolve 100 mg of 12,13-desepoxy-12,13-dehydrorosamicin (trans isomer) in 0.4 ml of acetone and add 45 mg of sodium bicarbonate and 0.025 ml of benzoyl chloride. Stir the mixture at room temperature for three days, then evaporate the solvent and triturate the residue with 1% aqueous ammonium hydroxide. Isolate the product by filtration and dry, m.p. 108°-111°, $[\alpha]_D-2.5°$ (ethanol), $\lambda_{max}^{MeOH}$ 228 nm ($\epsilon$16,300), 283 nm ($\epsilon$20,500), mass spectrum M+ 669.

EXAMPLE 7

12,13-Desepoxy-12,13-dehydrorosamicin-2'-stearate

To a solution of 63 mg of stearoyl chloride in 0.5 ml of acetone, add 102 mg of 12,13-desepoxy-12,13-dehydrorosamicin and 50 mg of sodium bicarbonate. Stir the mixture at room temperature for two days, then remove the solids by filtration and evaporate the filtrate to a residue. Triturate the residue with dilute ammonium hydroxide and decant the aqueous phase from the resulting gum. Take up the latter in acetone and concentrate in vacuo to a residue of the desired compound, $[\alpha]_D-9°$ (ethanol), $\lambda_{max}^{MeOH}$ 283 nm ($\epsilon$20,400), mass spectrum M+ 832.

EXAMPLE 8

12,13-Desepoxy-12,13-dehydrorosamicin-3,2'-diacetate

Dissolve 744 mg of 12,13-desepoxy-12,13-dehydrorosamicin in 10 ml of pyridine and add 400 mg of acetic anhydride. Stir at room temperature for 20 hours, then evaporate the solvent under reduced pressure and triturate the residue with ammonium hydroxide. Take the solids up in ethyl acetate, wash with aqueous sodium bicarbonate and dry over sodium sulfate. Concentrate the solution to a residue of the desired compound, m.p. 105°-107°.

In a similar manner, by substituting other acylating agents, such as propionic anhydride, benzoyl chloride and the like, for the acetic anhydride in the above procedure, the corresponding diesters such as the 3,2'-dipropionate, 3,2'-dibenzoate and the like are obtained.

EXAMPLE 9

12,13-Desepoxy-12,13-dehydrorosamicin-3-acetate

Stir a solution of 720 mg of the 3,2'-diacetate of Example 8 in a mixture of 10 ml of methanol and 4 ml of water at room temperature for 5 hr. Replace the solvent with ethyl acetate, wash with water, dry and concentrate to a residue of the desired compound, m.p. 95°-98°, $[\alpha]_D-4°$ (ethanol).

EXAMPLE 10

12,13-Desepoxy-12,13-dehydrorosamicin 20-oxime

Heat a solution of 100 mg of 12,13-desepoxy-12,13-dehydrorosamicin and 15 mg of hydroxylamine hydrochloride in 10 ml of ethanol containing one drop of pyridine under reflux for one hour. Replace the solvent by tetrahydrofuran-hexane and filter. Dilute the filtrate with hexane and isolate the resulting precipitate by filtration to obtain the compound of this example, m.p. 165°-167°, $[\alpha]_D-38°$ (ethanol).

EXAMPLE 11

10,11-Dihydrorosamicin

Hydrogenate 1.2 g of rosamicin in 45 ml of methanol containing 200 mg of 5% palladium on charcoal catalyst until the ultraviolet absorption at about 240 nm has disappeared. Filter the mixture and concentrate the filtrate to a residue of the compound of this example, m.p. 94°-95°, $[\alpha]_D-1°$ (ethanol).

EXAMPLE 12

10,11-Dihydrorosamicin-2'-acetate

React 580 mg of the compound of Example 11 with 145 mg of acetic anhydride in 15 ml of acetone according to the procedure of Example 5. Work up the reaction mixture as described in Example 5 to isolate the title compound, m.p. 86°-87°.

EXAMPLE 13

12,13-Desepoxy-10,11-dihydrorosamicin

Hydrogenate a solution of 150 mg of the compound of Example 1A in 10 ml of ethanol containing 35 mg of 5% palladium on charcoal catalyst until the ultraviolet absorption at about 283 nm has disappeared. Filter and concentrate the filtrate to a residue of the compound of this example, m.p. 78°-79°.

EXAMPLE 14

20-Dihydrorosamicin

Add a solution of 290 mg of rosamicin in one ml of tetrahydrofuran to 150 mg of lithium aluminum tri-t-butoxyhydride in one ml of tetrahydrofuran and stir. Add an additional 50 mg of the reducing agent and stir for 18 hr. Dilute with water and extract with chloroform, separate the organic layer, wash with water and concentrate to a residue of the desired compound, $\lambda_{max}^{MeOH}$ 239 nm ($\epsilon$12,700), mass spectrum M+ 583.

EXAMPLE 15

20-Dihydrorosamicin-3,20,2'-triacetate

Dissolve 30 mg of the compound of Example 14 in 1.0 ml of pyridine and add 0.1 ml of acetic anhydride, allow to stand at room temperature for 5 days. Concentrate to a residue under reduced pressure, triturate with 2% aqueous ammonium hydroxide. Isolate the resulting solid by filtration and dry to obtain the compound of this example, m.p. 93°–96°, $\lambda_{max}^{MeOH}$ 238 nm ($\epsilon$12,700).

EXAMPLE 16

12,13-Desepoxy-12,13-dehydrorosamicin-3,2'-dipropionate

Prepare the compound of this example by subjecting 10 g of 12,13-desepoxy-12,13-dehydrorosamicin to the action of 10 ml. of propionic anhydride and 50 mg of dimethylamino pyridine in 30 ml. of pyridine for four days at room temperature (25° C). Precipitate the product into 300 ml. of 2.5% sodium carbonate. Stir the suspension for 15 minutes, filter, wash the precipitate with water and dry at 50° C in vacuo.

Yield — 10.1g

Dissolve 4g of the product of this example in chloroform and pass the solution through 50 g of silica gel collecting 60 ml. fractions. Combine fractions 8–16 and concentrate to a residue to obtain a purified sample of the product of this example.

Yield — 1.5g
[M +1]=676
$[\alpha]_D^{20°} = -12.5$ (c=0.3%, ethanol)
$\lambda_{max}^{MEOH}$ 283 nm ($\epsilon$=22,300)

EXAMPLE 17

2,3-Dehydro-3-deoxyrosamicin

A. Dissolve 2.75 g of rosamicin-2'-propionate in 40 ml of pyridine and add 1 ml of methanesulfonyl chloride. Allow the solution to stand at room temperature for 3 days. Evaporate the solution to a residue and triturate the residue with 1% ammonium hydroxide and then with hexane. Suspend the solid product in chloroform and pass the suspension through 42 g of silica gel. Concentrate the chloroform solution to a residue and obtain thereby 1 g of rosamicin-2'-propionate-3-methanesulfonate.

B. Dissolve 400 mg of the product of step A and 120 ml of pyridine and reflux for 4 hours. Remove the solvent in vacuo to obtain a residue. Suspend the residue and dilute (1%) ammonium hydroxide and extract with chloroform. Concentrate the chloroform solution to a residue, dissolve the residue in 10 ml of 80% aqueous methanol and reflux for 1 hour. Evaporate the solvent to obtain a residue, triturate the residue with chloroform and pass the chloroform suspension through 4 g of silica gel. Concentrate the chloroform solution and obtain 131 mg of the product of this Example having the following physical constants:

m.p. 104°–110° C
$[\alpha]_D^{26} = -39.1$ (0.3% ethanol)

EXAMPLE 18

2,3:12,13-Bisdehydro-3-deoxy-12,13-desepoxy rosamicin

A. Dissolve 475 mg of 12,13-desepoxy-12,13-dehydro rosamicin-2'-propionate in 5 ml of pyridine, add 0.25 ml of methanesulphonyl chloride and permit the solution to stand at room temperature for 6 days. Concentrate the solution to a residue and triturate the residue with 1% ammonium hydroxide. Filter the solids obtained thereby and dry in vacuo to obtain 790 mg of 12,13-desepoxy-12,13-dehydro rosamicin-2'-propionate-3-methanesulphonate.

B. Dissolve 480 mg of the product of step A in 100 ml of pyridine and reflux for 2 hours. Evaporate the solvent and suspend the resulting residue in dilute (1%) ammonium hydroxide. Extract the suspension with chloroform and concentrate the extract to a residue. Dissolve the residue in 20 ml of 80% aqueous methanol and reflux the solution for 1 hour. Concentrate the solution to a residue and chromatograph the residue on 46 g of silica get using a solvent system consisting of 3 parts methanol by volume to 97 parts chloroform to obtain the title product.

131 mg M.P. 98°–103° C
$[\alpha]_D^{26} = -21.9$ (0.3% ethanol)

EXAMPLE 19

Rosamicin 20-oxime

Heat a solution of 300 mg of rosamicin and 40 mg NH$_2$OH.HCl in 20 ml of ethanol containing a drop of pyridine under reflux for 3 hours. Evaporate the solvent under reduced pressure, dissolve the residue in 5 ml of tetrahydrofuran, filter and add hexane to precipitate the compound of this example, which is isolated by filtration, m.p. 158°–161°, $[\alpha]_D^{26°}$ −26.2 (c=0.3% ethanol)

EXAMPLE 20

Rosamicin-20-dimethylacetal

Dissolve 1.0g of rosamicin in 10 ml. of methanol, add 1.0 ml. of difluoroacetic acid, attach a drying tube and allow the reaction mixture to stand at room temperature (25° C) for 72 hours. Concentrate the reaction mixture to about ½ the original volume and precipitate into 50 ml. of 10% sodium bicarbonate solution. Filter the suspension and dry the precipitate in vacuo at 40° C.

Yield = 0.8g $[\alpha]_D^{26} = -17.5$ (c = 0.3%, ethanol)
$\lambda_{max}^{ME\ OH}$ 240 nm ($\epsilon$ =13,650)

EXAMPLE 21

9-Dihydro-rosamicin-20-dimethylacetal

Dissolve 8.9g of rosamicin 20-dimethylacetal (prepared as described in the preceding example) in 90 ml. of methanol and add 2.5g of sodium borohydride portionwise over a five minute interval. Stir the reaction mixture for an additional 20 minutes during which time an exothermic reaction takes place. Dilute the reaction mixtue with 500 ml. of chloroform and shake with 200 ml of 5% sodium bicarbonate solution. Separate the solvent layer and concentrate the chloroform layer to a residue. Chromatograph the residue on 700 g of silica gel using as the eluant a solvent system consisting of toluene, chloroform methanol and conc. ammonium hydroxide in the volume ratio of 3:1:0.5:.025 to obtain thereby the compound of this example.

Yield — 5.9g.

EXAMPLE 22

10,11-Dihydroxy-10,11-dihydrorosamicin

A. Dissolve 2.92 g of rosamicin and 1.3 g of osmium tetroxide in 15 ml of pyridine and stir the mixture at room temperature (20°–25° C) for 5 hours. Add 2.5 g of sodium bisulfite dissolved in 25 ml of pyridine and 40 ml of water. Stir the mixture for one-half hour at room temperature. Extract the reaction mixture with chloroform and replace the chloroform with ethyl acetate. Wash the ethyl acetate solution with a solution of ammonium sulfide in dilute ammonium hydroxide, then wash with water and dry over anhydrous sodium sulfate. Filter and evaporate the filtrate to a residue. Yield 610 mgs.

B. Prepare a chromatographic column of 60 g of silica gel using a solvent system consisting of 3% methanol in chloroform $v/v$. Adsorb the residue from step A and elute with 4.0 liters of the solvent system followed by 4.0 liters of 5% methanol in chloroform while collecting 25 ml fractions. Combine fractions 49–72 containing a single component and evaporate to a residue to obtain the compound of this example.

Mass Spec. M+ = 615
U.V. no absorption beyond 220 nm

EXAMPLE 23

12,13-Desepoxy-12,13-dehydrorosamicin lauryl sulfate salt

Dissolve 50 mg. of 12,13-desepoxy-12,13-dehydrorosamicin in 0.5 ml of acetone and dissolve 25.5 mg of sodium lauryl sulfate in 5.0 ml of water. Add to the solution 0.01 ml of acetic acid and stir under a nitrogen atmosphere for about 45 minutes to permit the acetone to evaporate. Refrigerate the oily residue overnight then decant off the water. Triturate the oily residue with hexane and refrigerate for 2 hours. Decant off the hexane and triturate with ethanol followed by decantation of the solvent. Dry the resulting product at about 40° C in vacuo to obtain the compound of this example. Yield — 60 mg M.P. 129°–132° C $[\alpha]_D^{26°} = -15.4°$ C = 0.3% ethanol $\lambda_{283}^{MeOH}$ nm ($\epsilon$ = 21,000)

In an analogous manner, by substituting an equivalent quantity of other sodium alkyl sulfates such as sodium tetradecyl sulfate, sodium hexadecyl sulfate, sodium octadecyl sulfate for sodium lauryl sulfate, and by following the procedure of Example 23, the following compounds may be prepared:

12,13-desepoxy-12,13-dehydrorosamicin tetradecyl sulfate salt, 12,13-desepoxy-12,13-dehydrorosamicin hexadecyl sulfate salt, and 12,13-desepoxy-12,13-dehydrorosamicin octadecyl sulfate salt.

In a similar manner by substituting an equivalent quantity of the following compounds or esters thereof and by substituting an equivalent quantity of the above-named sodium alkyl sulfate salts and by subjecting them to the process of Example 23, the analogous alkyl sulfate salts may be prepared: 10,11-dihydroxy-10,11-dihydrorosamicin,10,11-dihydrorosamicin, 12,13-desepoxy-10,11-dihydrorosamicin, 20-dihydrorosamicin and 2,3-dehydro-3-deoxyrosamicin.

EXAMPLE 24

12,13-Desepoxy-12,13-dehydrorosamicin-20-dimethylacetal

A. Dissolve 10 g of 12,13-desepoxy-12,13-dehydrorosamicin in 100 ml of methanol and add 6 ml of difluoroacetic acid. Allow the reaction mixture to stand at room temperature (25° C) for 72 hours. Concentrate the reaction mixture to 50 ml and precipitate into 500 ml of 10% sodium bicarbonate. Filter the suspension and dry the precipitate at 50° C in vacuo to obtain thereby the compound of this example.

Yield — 10.5 g
$\lambda_{max}^{MEOH}$ 283 nm ($\epsilon$ = 21,265)

B. Dissolve 1.0 g of the product from step A in chloroform and chromatograph on 100g of silica gel using 5% methanol in chloroform as the eluant. Combine fractions 28–60.

Yield 0.65g
$[\alpha]_D^{26°} = 1.3$ (c = 0.3%, ethanol)
$\lambda_{max}^{MEOH}$ 283 nm ($\epsilon$ = 22,480)

In a similar manner, treat an equivalent quantity of the following compounds to the process of Example 24:
10,11-dihydrorosamicin,
12,13-desepoxy-10,11-dihydrorosamicin,
2,3-dehydro-3-deoxyrosamicin,
2,3:12,13-bisdehydro-3-deoxy-12,13-desepoxyrosamicin, and
10,11-dihydroxy-10,11-dihydrorosamicin.

Isolate the respective products as described in Example 24 to obtain thereby the following compounds:
10,11-dihydrorosamicin-20-dimethylacetal,
12,13-desepoxy-10,11-dihydrorosamicin-20-dimethylacetal,
2,3-dehydro-3-deoxyrosamicin-20-dimethylacetal,
2,3:12,13-bisdehydro-3-deoxy-12,13-desepoxyrosamicin-20-dimethylacetal and
10,11-dihydroxy-10,11-dihydrorosamicin-20-dimethylacetal, respectively.

EXAMPLE 25

9-Dihydro-12,13-desepoxy-12,13-dehydrorosamicin-20-dimethyl-Acetal

Dissolve 6.0 g. of 12,13desepoxy-12,13-dehydrorosamicin 20-dimethylacetal in 60 ml. of methanol. Add 3.5 g. of sodium borohydride and stir for 30 minutes. Dilute with 10 volumes of chloroform and shake the resulting solution with 10% sodium carbonate solution, wash the chloroform layer with water and concentrate to a residue. Dissolve the residue in chloroform and adsorb the product on 100 g. of silica gel. Elute the silica gel column with 1.0 liters of chloroform, then with 5% methanol in chloroform. Combine fractions 63–105 and concentrate to a residue to obtain thereby the product of this example.

Yield — 3.7 g. $[\alpha]_D^{26} = +2.0$ (c=9.3%, ethanol)
$\lambda_{max}^{MEOH}$ 238 nm ($\epsilon$ = 24,431) M + 613

In a similar manner, treat an equivalent quantity of products set forth after Example 24 to the process of Example 25 and obtain thereby the following compounds:
9-dihydro-10,11-dihydrorosamicin-20-dimethylacetal,
9-dihydro-12,13-desepoxy-10,11-dihydrorosamicin-20-dimethylacetal,
9-dihydro-2,3-dehydro-3-deoxyrosamicin-20-dimethylacetal, 9-dihydro-2,3:12,13-bisdehydro-3-deoxy-12,13-desepoxyrosamicin-20-dimethylacetal, and
9-dihydro-10,11-dihydroxy-10,11-dihydrorosamicin-20-dimethylacetal, respectively.

EXAMPLE 26

9-Dihydro-12,13-desepoxy-12,13-dehydrorosamicin

Dissolve 3.3 g. of the product of the preceding example in a mixture of 30 ml. of acetonitrile and 30 ml. of water, add 1.0 ml. of trifluoroacetic acid and let stand at room temperature for 5 hours. Dilute with 150 ml. of chloroform, shake with 10% sodium carbonate solution. Extract the aqueous layer with fresh chloroform. Combine the chloroform layers, wash with water and concentrate to a residue. Dissolve the residue in a mixture of toluene, chloroform, methanol and conc. ammonium hydroxide in the volume ratio of 3:1:0.5:0.25 and chromatograph on 240 g. of silica gel using the same solvent mixture as eluant. Combine fractions 49-73 to obtain the product of this example.

Yield — 2.15 g. $[\alpha]_D^{26°} = -3.2°$ (c = 0.3% ethanol)
$[M + 1]^{30} = 567$ $\lambda_{max}^{MEOH}$ 238 nm ($\epsilon = 20,180$)

In a similar manner, treat an equivalent quantity of the products set forth after Example 25 to the process of Example 26 and obtain thereby the following compounds:

9-dihydro-10,11-dihydrorosamicin,
9-dihydro-12,13-desepoxy-10,11-dihydrorosamicin,
9-dihydro-2,3-dehydro-3-deoxyrosamicin,
9-dihydro-2,3:12,13-bisdehydro-3-deoxy-12,13-desepoxyrosamicin, and
9-dihydro-10,11-dihydroxy-10,11-dihydrorosamicin, respectively.

In like manner, the product of Example 21 i.e. 9-dihydro-rosamicin-20-dimethylacetal may, by the process of Example 26, be converted to 9-dihydrorosamicin.

EXAMPLE 27

12,15-Desepoxy-12,13-dehydrorosamicin-3-propionate

Dissolve 7.4 g of 12,13-desepoxy-12,13-dehydrorosamicin-3,2'-dipropionate (prepared as described in Example 16) in 150 ml of 80% methanol-water. Allow the reaction to stand at room temperature (25° C) for 3 days. Concentrate the reaction mixture to about 40 ml and precipitate into 400 ml of 5% sodium bicarbonate. Filter the suspension, wash sparingly with water and dry the precipitate at 50° C in vacuo. Dissolve the product in chloroform and chromatograph on 600 g of silica gel elute with chloroform collecting the first 3.0 l. of chloroform, then switching to 4% methanol in chloroform. Combine fractions 168 to obtain 320 and concentrate to a residue to obtain thereby the compound of this example.

Yield 3.0 g $[\alpha]_D^{26°} = -8.4$
(c=0.3%, ethanol)
$(M + 1)^+ = 622$

EXAMPLE 28

20-Dihydro-12,13-desepoxy-12,13-dehydrorosamicin

A. Dissolve 0.9 g of 12,13-desepoxy-12,13-dehydrorosamicin (prepared as described in Example 1) in 3 ml of tetrahydrofuran and add 660 mg of lithium tri-t-butoxy aluminum hydride in 3 ml of tetrahydrofuran. Stir the reaction mixture at room temperature (25° C) for 20 minutes. Add an additional 1.5 g of the reducing agent portionwise and allow the reaction to proceed overnight (16 hours). Dilute the reaction mixture with 100 ml of chloroform and shake with 50 ml of aqueous sodium bicarbonate. Wash the chloroform solution with water, concentrate and replace with ethyl alcohol. Concentrate the alcoholic solution with the addition of water and lyophilize to obtain the product of this Example.

Yield 0.5 g

B. Dissolve 0.59 g of 20-dihydro-12,13-desepoxy-12,13-dehydrorosamicin (prepared as described in step A) in chloroform and chromatograph on 50 g of silica gel using 4% methanol in chloroform as the eluant. Combine fractions 91-150 to obtain purified 20-dihydro-12,13-desepoxy-12,13-dehydrorosamicin.

M + 567
$\lambda_{max}^{MEOH}$ 283 nm ($\epsilon = 19,830$)

In general, the compounds of this invention are more effective against gram-positive organisms. However, they also have activity against gram-negative species. Exemplary of the organisms against which the compounds of this invention may be used are strains of such species as *Staphylococcus aureus, Streptococcus pyogenes, Bacillus subtilis, Escherichia coli, proteus vulgaris, Pseudomonas aeruginosa* and the like.

Set forth hereinbelow are examples directed to some of the dosage forms wherein the compounds of this invention including non-toxic pharmaceutically acceptable acid addition salts, non-toxic pharmaceutically acceptable esters and non-toxic pharmaceutically acceptable acid addition salts of said esters may be employed. The formulations, excluding the topicals, are designed to permit the administration of from about 5 to about 50 mg. of antibiotic (as the free base) per kilogram of body weight per day. For topical application, the formulations are designed to contain from about 0.5 to about 2% of antibacterial agent. The topical formulations are generally applied to the infected area from about 2 to about 4 times daily. It should be noted, however, that the size of the dosage administered and the frequency thereof depend to a great extent upon the type of infection, its severity and the individual characteristics of the animal species being treated. The compounds of this invention are especially well-suited for treating warm-blooded animals but may also be used for such in vitro purposes as disinfectants for laboratory glassware, dental and medical equipment.

Example 29

| Capsule | |
|---|---|
| 12,13-Desepoxy-12,13-dehydrorosamicin | 250.00 mg. |
| Lactose | 248.75 mg. |
| Magnesium Stearate | 1.25 mg. |
| | 500.00 mg. |

Procedure:

1. Blend the antibacterial agent and the lactose
2. Add the magnesium stearate and mix
3. Fill capsule

Example 30

| Oral Suspension (to give a dose of 125 mg/5 ml) | |
|---|---|
| 12,13-Desepoxy-12,13-dehydrorosamicin-2'-benzoate | 25.00 gms. |
| Magnesium aluminum silicate | 9.5 gms. |
| Sodium Carboxymethylcellulose, U.S.P. | 2.5 gms. |
| Sodium Citrate, U.S.P. | 25.0 gms. |
| Flavor | q.s. |
| Color | q.s. |
| Methylparaben, U.S.P. | 0.9 gms. |
| Propylparaben, U.S.P. | 0.2 gms. |
| Polysorbate 80, U.S.P. | 1.0 gms. |
| Sorbitol Solution, U.S.P. | 500.0 gms. |

Example 30-continued

Oral Suspension (to give a dose of 125 mg/5 ml)

| | |
|---|---|
| Water q.s. | 1000.0 ml. |

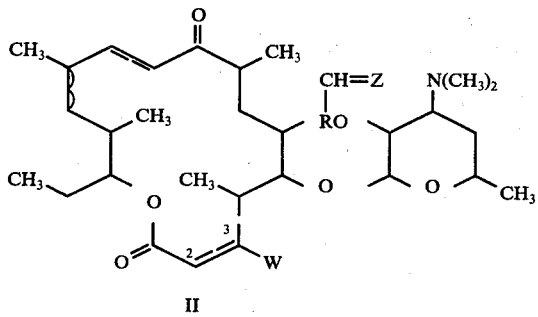

II

Procedure:

1. Heat 200 ml. of water to boiling, and dissolve in it one half of the parabens. Cool to about 70° C, then mix in the Polysorbate 80. Sprinkle in the silicate, stirring until a uniform smooth suspension results.

2. Heat an additional 200 ml. of water to boiling, and dissolve in it the remainder of the parabens. Disperse the CMC in this until a smooth gel results. Mix in the Sorbitol Solution. Then dissolve the sodium citrate.

3. Add the product of Step 2 to that of Step 1 slowly, with constant stirring. Cool the mixture to 25° C. Add the antibacterial agent, tartrate flavor, and color and mix thoroughly. Add water to a total volume of 1000 ml.

Example 31

| Topical Cream: | |
|---|---|
| 12,13-Desepoxy-12,13-dehydrorosamicin-2'-propionate | 10 gm. |
| Stearic Acid | 200 gm. |
| Sorbitan Monostearate | 104 gm. |
| Sorbitan Monoleate | 20 gm. |
| Polyoxyethylene Sorbitan Monolaurate | 56 gm. |
| Water q.s. | 1000 ml. |

Procedure:

1. Heat the stearic acid, sorbitan monostearate, sorbitan monoleate, and polyoxyethylene sorbitan monolaurate to 65° C.

2. Heat about 90% of the water to 70° C.

3. Add the water to Step 1 and mix to form the cream base.

4. Slurry the antibacterial agent with about 10% of the water and pass through a colloid mill.

5. Add the milled slurry to the molten base and mix. Allow to cool.

Example 32

| Topical Ointment | |
|---|---|
| 12,13-Desepoxy-12,13-dehydrorosamicin-2'-stearate | 10 gm. |
| Petrolatum | 990 gm. |
| | 1000 gm. |

Procedure:

1. Melt the petrolatum.
2. Slurry the antibacterial agent with about 10% of the petrolatum and pass through a colloid mill.

3. Mix the milled slurry with the remainder of the molten petrolatum. Allow to cool.

We claim:

1. A compound of the formulae:

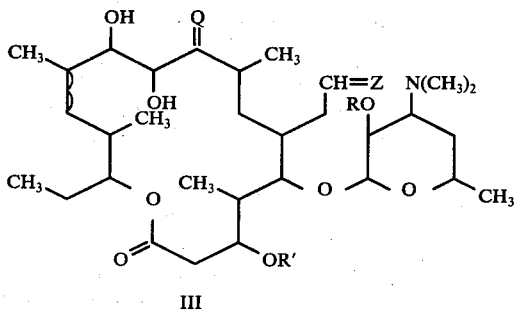

III and the non-toxic pharmaceutically acceptable acid addition salts thereof wherein the dotted lines represent facultative double bonds; Q is a member selected from the group consisting of O, and $$\left\langle \begin{array}{l} OR' \\ H; \end{array} \right.$$

Z is a member selected from the group consisting of O,

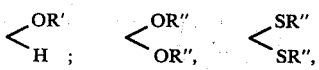

NOR' and NOR''; R and R' are members selected from the group consisting of hydrogen and hydrocarbon carbonyl having 2 to 18 carbon atoms; R'' is hydrogen or alkyl having 1 to 5 carbon atoms; B together with the carbon atoms of positions 12 and 13 to which it is attached represents a single bond or a double bond or, when Q or Z is other than O, or when the macrolide ring is saturated between positions 10 and 11 or unsaturated between positions 2 and 3, B may also be an oxirane ring; and W is a member selected from the group consisting of OR' and hydrogen, R' being as previously defined with the proviso that when W is hydrogen, positions 2 and 3 are connected by a double bond, and the further proviso that in formula II, when B, together with the carbon atoms to which it is attached represents a double bond, W is OR', Q is O, and positions 10 and 11 are connected by a double bond, Z is other than $$\left\langle \begin{array}{l} OR' \\ H. \end{array} \right.$$

2. A compound of claim 1 of the formula:

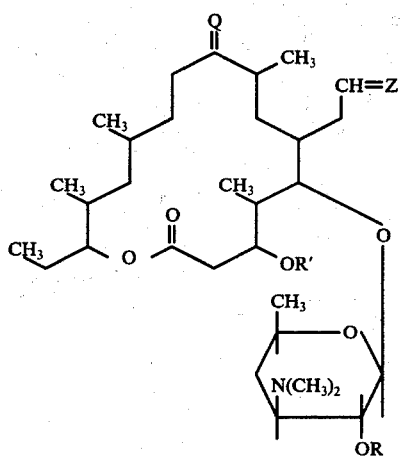

wherein Z, R, and R' are as defined in claim 1.

3. A compound of claim 1, formula II, having the formula:

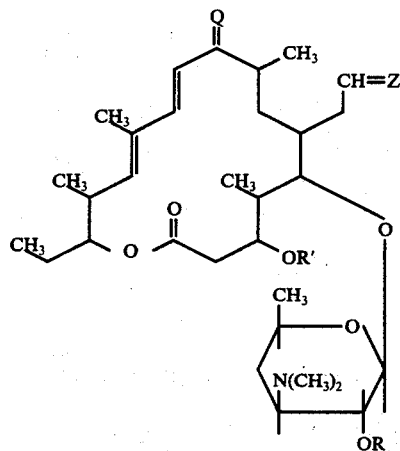

wherein Q, Z, R and R' are as defined in said claim 1, with the proviso that when Q is O, Z is other than

4. A compound of claim 1 of the formula:

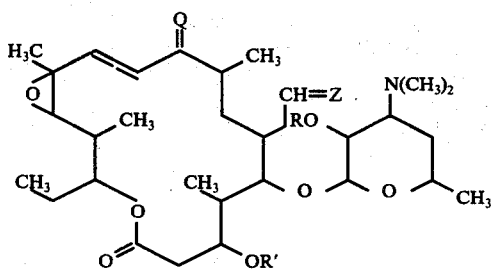

wherein Q,Z,R and R' are as defined in said claim 1.

5. A compond of claim 1 of the formula:

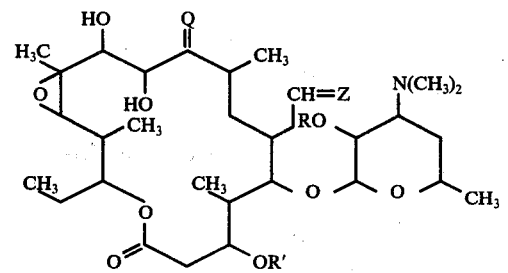

wherein Q,Z, R and R' are as defined in said claim 1.

6. A compound of claim 1 of the formula:

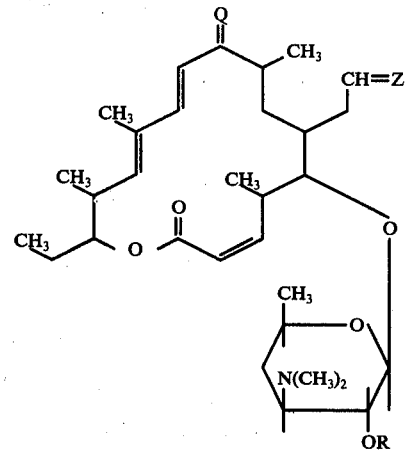

wherein Q,Z and R are as defined in said claim 1.

7. A compound of claim 1 of the formula:

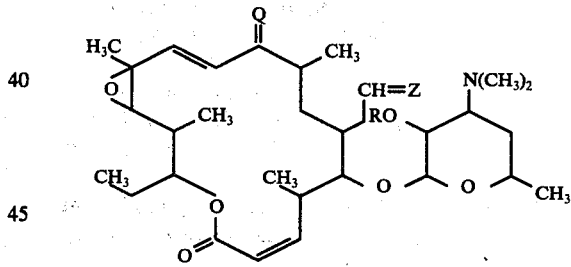

wherein Q, Z and R are as defined in said claim 1.

8. A non-toxic acid addition salt of a compound of claim 2.

9. A compound of claim 8, said compound being the lauryl sulfate salt of 12,13-desepoxy-10,11-dihydrorosamicin.

10. The compound of claim 2 wherein Q is

R and R' are hydrogen and Z is O, said compound being 9-dihydro-12,13-desepoxy-10,11-dihydrorosamicin.

11. A compound of claim 2 wherein Q is

R and R' are hydrogen and Z is

12. The compound of claim 11 wherein Z is

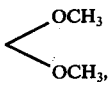

said compound being 9-dihydro-12,13-desepoxy-10,11-dihydrorosamicin-20-dimethylacetal.

13. A compound of claim 2 wherein Q is O, R and R' are hydrogen and Z is

14. The compound of claim 13, wherein Z is

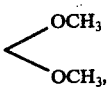

said compound being 12,13-desepoxy-10,11-dihydrorosamicin-20-dimethylacetal.

15. A compound of claim 3, wherein Q and Z are O, R and R' are hydrogen, said compound being 12,13-desepoxy-12,13-dehydrorosamicin.

16. A non-toxic acid addition salt of a compound of claim 15.

17. A compound of claim 16 wherein the acid is stearic acid, said compound being 12,13-desepoxy-12,13-dehydrorosamicin stearate salt.

18. A compound of claim 16 wherein the acid is phosphoric acid, said compound being 12,13-desepoxy-12,13-dehydrorosamicin potassium dihydrogen phosphate salt.

19. A compound of claim 16, said compound being the lauryl sulfate salt of 12,13-desepoxy-12,13-dehydrorosamicin.

20. A compound of claim 3 wherein Q is

Z is O, R and R' are hydrogen, said compound being 9-dihydro-12,13-desepoxy-12,13-dehydrorosamicin.

21. A compound of claim 3 wherein R is hydrocarbon carbonyl having 2 to 18 carbon atoms, R' is hydrogen, and Q and Z are O.

22. The compound of claim 21 wherein R is propionyl, said compound being 12,13-desepoxy-12,13-dehydrorosamicin 2'-propionate.

23. The compound of claim 21 wherein R is acetyl, said compound being 12,13-desepoxy-12,13-dehydrorosamicin 2'-acetate.

24. The compound of claim 21 wherein R is benzoyl, said compound being 12,13-desepoxy-12,13-dehydrorosamicin 2'-benzoate.

25. The compound of claim 21 wherein R is steroyl, said compound being 12,13-desepoxy-12,13-dehydrorosamicin 2'-stearate.

26. A compound of claim 3 wherein R and R' are hydrocarbon carbonyls having 2 to 18 carbon atoms and Q and Z are O.

27. The compound of claim 26 wherein R and R' are acetyl, said compound being 12,13-desepoxy-12,13-dehydrorosamicin 3,2'-diacetate.

28. A compound of claim 3 wherein R is hydrogen, R' is hydrocarbon carbonyl having 2 to 18 carbon atoms and Q and Z are O.

29. The compound of claim 28 wherein R' is acetyl, said compound being 12,13-desepoxy-12,13-dehydrorosamicin 3-acetate.

30. A compound of claim 4 wherein Q is O; R and R' are hydrogen and positions 10 and 11 are joined by a single bond, said compound being 10,11-dihydrorosamicin.

31. A compound of claim 4 wherein Q, R and R' are as defined in said claim and Z is

32. The compound of claim 31 wherein Q is O; R and R' are hydrogen and positions 10 and 11 are joined by a double bond, said compound being 20-dihydrorosamicin.

33. The compound of claim 4 wherein Q is O; R and R' are acetyl and Z is

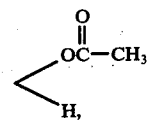

and positions 10 and 11 are joined by a double bond, said compound being 20-dihyrorosamicin-3, 20,2'-triacetate.

34. A compound of claim 4 wherein Q, R, and R' are as defined in said claim, Z is NOR" and positions 10 and 11 are joined by a double bond.

35. The compound of claim 34 wherein Q is O; R, R' and R" are hydrogen, said compound being rosamicin-20-oxime.

36. A compound of claim 4 wherein Q, R, and R' are as defined in said claim, Z is

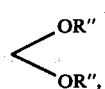

and positions 10 and 11 are joined by a double bond.

37. The compound of claim 36 wherein Q is O; R and R' are hydrogen and R" is methyl, said compound being rosamicin-20-dimethylacetal.

38. The compound of claim 36 wherein Q is

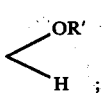

R and R' are hydrogen and R" is methyl, said compound being 9-dihydrorosamicin-20-dimethylacetal.

39. A compound of claim 4 wherein Q is

Z, R and R' are as defined in said claim.

40. The compound of claim 39 wherein Z is O, R and R' are hydrogen, said compound being 9-dihydrorosamicin.

41. A compound of claim 5 wherein Q and Z are O and R and R' are as defined in said claim.

42. The compound of claim 41 wherein R and R' are hydrogen, said compound being 10,11-dihydroxy-10,11-dihydrorosamicin.

43. A compound of claim 6 wherein Q and Z are O and R is as defined in said claim.

44. The compound of claim 43, wherein R is hydrogen, said compound being 2,3:12,13-bisdehydro-3-deoxy-12,13-desepoxy-rosamicin.

45. A compound of claim 7 wherein Q and Z are O and R is as defined in said claim.

46. The compound of claim 45 wherein R is hydrogen, said compound being 2,3-dehydro-3-deoxyrosamicin.

47. A method of eliciting an antibacterial response which comprises administering to a warm-blooded animal having a bacterial infection a therapeutically effective quantity of a compound of the formulae:

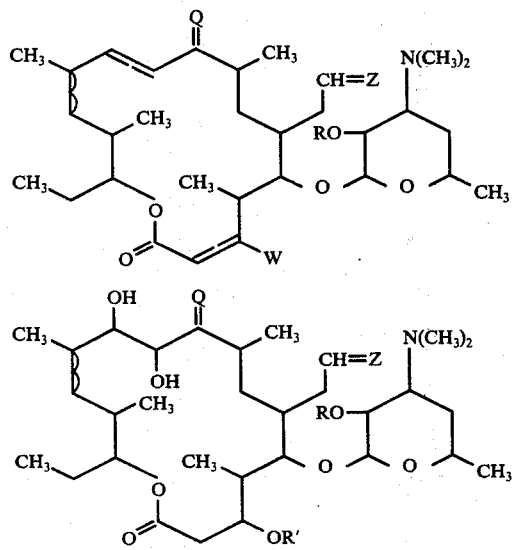

the non-toxic pharmaceutically acceptable acid addition salts thereof wherein the dotted lines represent facultative double bonds; Q is a member selected from the group consisting of O, and

Z is a member selected from the group consisting of O,

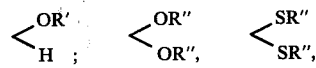

NOR' and NOR"; R and R' are members selected from the group consisting of hydrogen and hydrocarbon carbonyl having 2 to 18 carbon atoms; R" is hydrogen or alkyl having 1 to 5 carbon atoms; B together wtih the carbon atoms of positions 12 and 13 to which it is attached represents a single bond or a double bond or, when Q or Z is other than O, or when the macrolide ring is saturated between positions 10 and 11 or unsaturated between positions 2 and 3, B may also be an oxirane ring; and W is a member selected from the group consisting of OR' and hydrogen, R' being as previously defined with the proviso that when W is hydrogen, positions 2 and 3 are connected by a double bond, and the further proviso that in formula II, when B, together with the carbon atoms which it is attached represents a double bond, W is OR', Q is O, and positions 10 and 11 are connected by a double bond, Z is other than

48. A method according to claim 47 wherein the compound is administered at a dosage range of from about 5 mg to about 50 mg per kilogram of body weight per day.

49. A method according to claim 47 wherein the anti-bacterial response is effected by oral administration.

50. A method according to claim 47 wherein the anti-bacterial response is effected by topical administration.

51. A method according to claim 47 wherein the anti-bacterial response is effected by parenteral administration.

* * * * *

UNITED STATES PATENT OFFICE
CERTIFICATE OF CORRECTION

Patent No. 4,056,616        Dated  November 1, 1977

Inventor(s)  H. Reimann, R. Jaret, M. M. Nafissi-Varchei

It is certified that error appears in the above-identified patent and that said Letters Patent are hereby corrected as shown below:

Column 18, line 16, "790 mg." should read --490 mg--.
Column 20, line 57, "($\underline{C}$ = 9.3%," should read --($\underline{C}$ = 0.3%,--.
Column 21, line 22, "$[\bar{M} + 1]30$" should read --$[\bar{M} + 1]^+$--.
Column 25, line 21 (Claim 2) "wherein Z, R and R'" should read --wherein Q, Z, R and R'--.

*Signed and Sealed this*

*Twenty-first* Day of *March 1978*

[SEAL]

Attest:

RUTH C. MASON
*Attesting Officer*

LUTRELLE F. PARKER
*Acting Commissioner of Patents and Trademarks*